United States Patent [19]
Tanihata et al.

[11] Patent Number: 5,900,557
[45] Date of Patent: May 4, 1999

[54] AUTOMATIC SAMPLE TREATMENT APPARATUS

[75] Inventors: Hiroshi Tanihata; Masahito Ueda, both of Kyoto, Japan

[73] Assignee: Shimadzu Corporation, Kyoto, Japan

[21] Appl. No.: 08/888,649

[22] Filed: Jul. 7, 1997

[30] Foreign Application Priority Data

Sep. 30, 1996 [JP] Japan .................................... 8-280245

[51] Int. Cl.⁶ ..................................................... G01N 1/10

[52] U.S. Cl. .................................... 73/863.01; 73/864.01; 73/864.31; 422/67; 141/130; 198/339.1; 198/345.1

[58] Field of Search ........................... 73/863.01, 863.02, 73/863.03, 864.01, 864.31; 422/100, 63, 64, 65, 66, 67; 141/130; 198/345.1, 339.1

[56] References Cited

U.S. PATENT DOCUMENTS

| | | | |
|---|---|---|---|
| 4,854,355 | 8/1989 | Chazot et al. | 73/863.01 |
| 4,947,695 | 8/1990 | Lohr | 73/863.01 |
| 5,380,666 | 1/1995 | Wuerschum | 422/63 |
| 5,411,065 | 5/1995 | Meador et al. | 422/63 |
| 5,582,795 | 12/1996 | Nishina et al. | 422/63 |

*Primary Examiner*—Hezron Williams
*Assistant Examiner*—Nashmiya Fayyaz
*Attorney, Agent, or Firm*—Kanesaka & Takeuchi

[57] ABSTRACT

In an automatic sample treatment apparatus of the invention, a tray for vials is provided with slits for a home position and vial positions. The slits for the vial positions have shapes different from that of the slit for the home position. When the apparatus is used, a position detecting sensor detects a desired sample position, and a vial detecting sensor recognizes that the vial is disposed. Then, a syringe is lowered to suck a sample from a vial. Accordingly, even if a stepping motor becomes out of tune, the tray can be transferred to a position in which a needle is securely inserted into the vial.

8 Claims, 4 Drawing Sheets

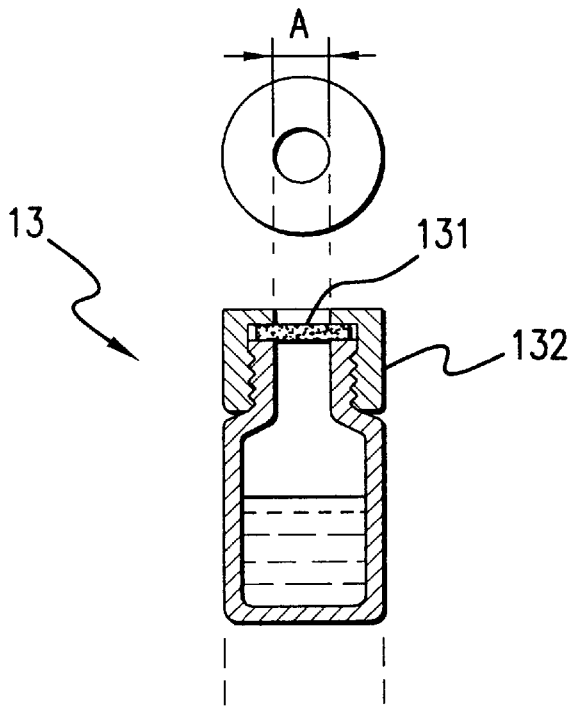
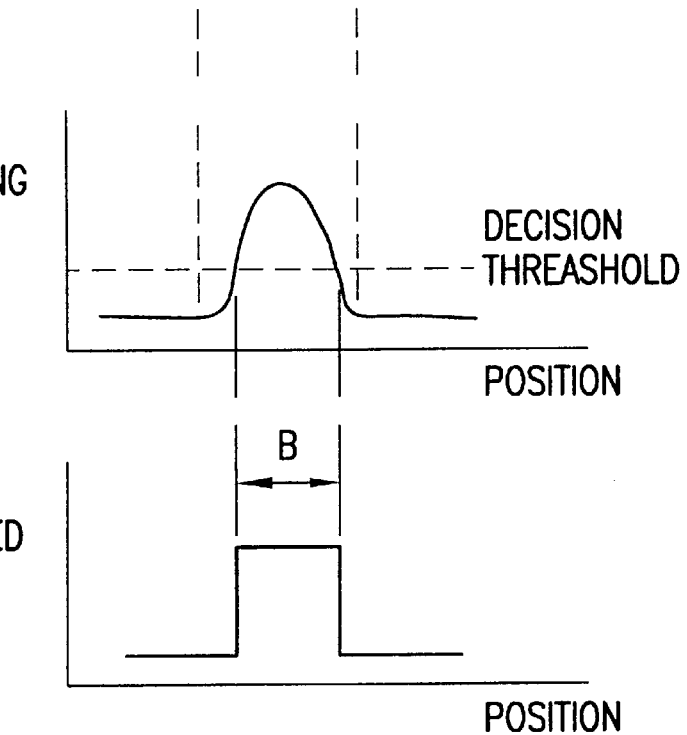
FIG.4(a)
FIG.4(b)
FIG.4(c)
FIG.4(d)

AUTOMATIC SAMPLE TREATMENT APPARATUS

BACKGROUND OF THE INVENTION AND RELATED ART STATEMENT

The present invention relates to an automatic sample treatment apparatus which is used in an analyzing apparatus, such as a gas chromatograph, a liquid chromatograph, and a spectrum analyzing apparatus.

In case a sample is analyzed in the analyzing apparatus, such as a gas chromatograph, usually, it is operated such that a syringe, which has the same structure as in an injector or a syringe as a medical instrument, sucks or draws a predetermined amount of a sample from a sample bottle or vial. In order to analyze a plurality of samples continuously, there is used an automatic sample treatment or injection apparatus, wherein a syringe is disposed above a tray holding a plurality of vials, and the predetermined vials are consecutively and automatically transferred to a position in which the syringe can suck a sample.

A structure of a main part of the automatic sample treatment or injection apparatus described above is shown in FIGS. 3(a) and 3(b). FIG. 3(a) is a front view of a conventional automatic sample injection apparatus, and FIG. 3(b) is a side view thereof.

The automatic sample injection apparatus is formed of a syringe 11; a syringe driving section 12 for vertically moving the syringe 11; a tray 24 for holding a plurality of vials 13; and a tray driving section 15 for slidingly transferring the tray 24. The syringe 11 is formed of a barrel 111; a needle 112 attached to a distal end of the barrel 111; and a plunger 113 inserted and fitted in the barrel 111. By a plunger driving section 19, the plunger 113 is pushed into or pulled out of the barrel 111. The tray driving section 15 is formed of a stepping motor 151; a pinion 152 fixed to a rotation axis of the stepping motor 151; and a rack 153 which is provided in the tray 24 and engaged with the pinion 152. Also, a slit 241 is formed at an end portion of the tray 24, and in order to detect the slit 241, a home position sensor 26 including a light emission section and a light receiving section is provided in a predetermined position. Further, a vial detecting sensor 17 is disposed in front of the tray 24 to be vertically aligned with the syringe 11 (FIG. 3(a)).

Operations of the automatic sample injection or treatment apparatus are as follows. Firstly, the tray 24 is moved to a predetermined standard position, i.e. home position, by the tray driving section 15. At this time, light emitted from the light emission section of the home position sensor 26 is reflected at a lower end surface of the tray 24, and the returned light is detected at the light receiving section, so that a position in which the reflected light is not received or obtained due to the slit 241 is recognized as a home position.

Thereafter, a pulse signal with a number corresponding to an amount of transfer from the home position to a desired vial position is applied to the stepping motor 151, so that the tray 24 is transferred. The vial detecting sensor 17 includes a light emission section and a light receiving section as in the home position sensor 26, wherein light emitted from the light emission section hits the vial for reflection, and the reflected light is detected at the light receiving section so as to determine the presence of the vial. After the tray 24 is transferred to locate the desired vial at the sample suction position just under the needle 112, if the vial detecting sensor 17 determines that there is a vial, the syringe driving section 12 lowers the syringe 11, so that the needle 112 is inserted into the vial 13. Then, the plunger 113 is pulled by the plunger driving section 19, and a liquid sample in the vial 13 is sucked into the barrel 111.

However, in the conventional automatic sample injection apparatus, since the transfer of the tray 24 is operated according to a relative position based on the home position, in case the stepping motor 151 becomes out of tune due to factors, such as an external force or load fluctuation of the tray 24, the following problems will occur.

FIGS. 4(a) through 4(d) show a relationship between the vial position and the detected signal of the vial detecting sensor, wherein FIG. 4(a) is a top plan view of the vial; FIG. 4(b) is a side section view of the vial; FIG. 4(c) shows an output at the light receiving section of the vial detecting sensor 17; and FIG. 4(d) shows a vial detecting signal obtained on the basis of the outputs of the light receiving section.

An opening on the upper surface of the vial 13 is smaller than an outer diameter of a lower part thereof, and at the opening on the upper surface, a septum 131 is tightened or attached by a resinous cap 132. An outer shape of the vial 13 is a column-like shape, and since the reflected light becomes weak as the position of the vial with respect to the vial detecting sensor 17 is deviated from a center of the vial, the output signal of the light receiving section of the vial detection sensor 17 provides a curve as shown in FIG. 4(c). By comparing the light receiving signal with a decision threshold which is set preliminarily, the detected signal showing a presence of a vial is formed as shown in FIG. 4(d).

In order to absorb a dispersion or deviation of the positions at the time of moving the tray 24 due to the individual difference of the apparatus or the like, it is required that the decision threshold is set at a comparatively low level so as to decide that there is a vial even if the position of the vial 13 is slightly deviated. Therefore, a range B for detecting a vial is wider than a sample absorbable range A, i.e. range in which the sample can be sucked, which substantially corresponds to the diameter of the opening of the upper surface of the vial 13.

As a result, in case the stepping motor 151 becomes out of tune and a deviation of X in the amount of transferring the tray 24 occurs, suction of a sample might be impeded. Namely, in case of X<A/2, suction is possible; but in case of A/2≦X≦B/2, it becomes highly possible that the needle 112 strikes the cap 132 of the vial 13 to cause bending of the needle. In case of B/2<X, the existence of the vial 13 itself can not be detected. When the needle 112 is broken, analysis thereafter can not be operated to cause extreme hinderance. Needless to say, there is also a problem such that it takes time to change the syringe 11 and it requires an additional cost.

Accordingly, the present invention is directed to solve the aforementioned problems, and an object of the present invention is to provide an automatic sample treatment or injection apparatus in which at the time of sucking the sample, a needle of a syringe can surely pierce a center of a septum of a vial, and especially, even if the stepping motor for driving the tray becomes out of tune, it can be prevented that the needle hits or strikes the vial itself.

Further objects and advantages of the invention will be apparent from the following description of the invention.

SUMMARY OF THE INVENTION

To achieve the above object, the present invention provides an automatic sample treatment apparatus for treating, i.e. sucking or injecting, a sample in a desired vial of a tray for holding a plurality of sample bottles or vials. The apparatus comprises position detecting means for detecting position markers which are formed in the tray to correspond to positions of the respective vials in the tray; driving means for transferring the tray; vial detecting means for detecting if there is a vial at a sample absorbable position; and control means. The control means controls the driving means to locate the desired vial at the sample absorbable position while determining a desired vial position by the position detecting means, and thereafter, the control means controls the syringe to operate for suction when the vial detecting means detects that there is a sample vial.

In the automatic sample treatment apparatus of the invention, the position detecting means is formed of, for example, slits provided in the tray at the appropriate positions corresponding to the respective vials, and a light sensor which is able to detect the slits and includes a light emission section and a light receiving section. The above described position detecting means recognizes the presence of the slit by light, which is emitted from the light emission section of the light sensor, reflected at a reflection surface of the tray and is detected at the light receiving section, to thereby decide whether it is a vial position or not.

The control means controls the driving means such that the tray is transferred in a predetermined direction, and the tray is stopped by a detected signal of the position detecting means when the desired vial position reaches at- the sample absorbable position (normally, just under the syringe). Then, whether there is in fact the sample vial at the desired vial position is detected by the vial detecting means, and if there is the vial, the syringe is lowered to suck the sample in the vial. Namely, in the conventional automatic sample injection apparatus, in order to transfer the tray to the desired vial position, an amount of transfer of the tray is controlled (open loop control) by the stepping motor. In contrast, in the automatic sample injection apparatus of the invention, positioning of the vial position is operated by the detection of the position marker by the position detecting means. Therefore, positioning of the vial position can be operated accurately.

In the automatic sample treatment of the invention, the vial position in the tray is securely detected, and the tray is stopped at a position wherein an opening of the vial is located in a sample absorbable range of the syringe. Therefore, it is possible to prevent an accident in which the needle of the vial inadvertently strikes a cap of the vial.

Furthermore, in the automatic sample injection apparatus of the invention, after the tray is moved so as to locate the desired vial at the sample absorbable range of the syringe, presence of the vial is detected, and in case the vial is not placed at the desired vial position, suction operation by the syringe is not performed. Therefore, useless operations of the syringe can be eliminated, and consecutive sample suction and injection operations can be effectively performed.

BRIEF DESCRIPTION OF THE DRAWINGS

FIGS. 1(a) and 1(b) show structural views of a main part of an automatic sample treatment or injection apparatus according to the invention, wherein FIG. 1(a) is a front view thereof, and FIG. 1(b) is a side view thereof;

FIGS. 4(a) through 4(d) show a relationship between a vial position and a detected signal of a vial detecting sensor, wherein FIG. 4(a) is a top plan view of a vial; FIG. 4(b) is a side sectional view of the vial; FIG. 4(c) shows an output of a light receiving section of the vial detecting sensor; and FIG. 4(d) shows a detected signal obtained on the basis of the output of the light receiving section.

DETAILED DESCRIPTION OF PREFERRED EMBODIMENTS

Figure 1A:
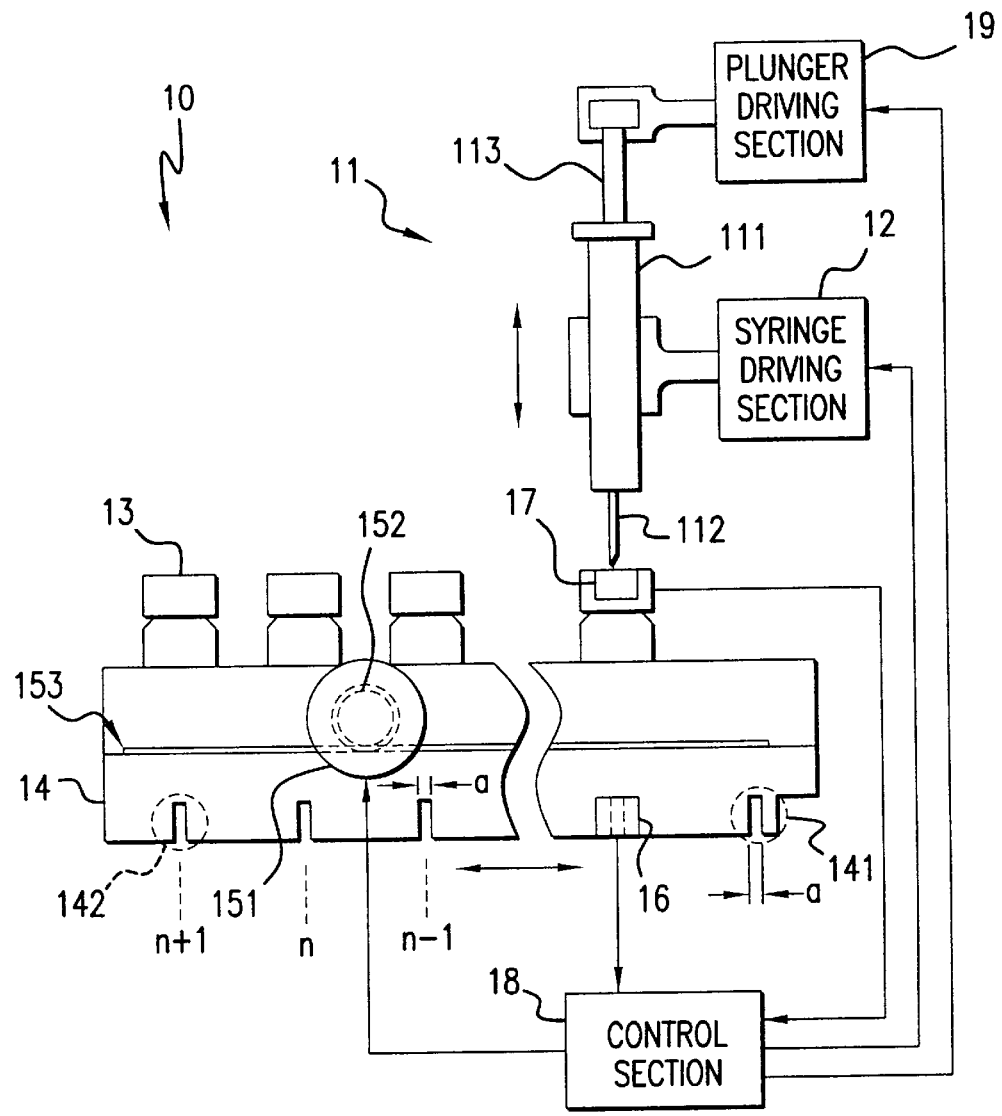
Figure 1B:
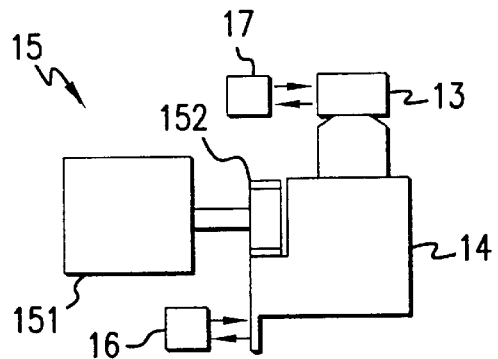
Figure 2:
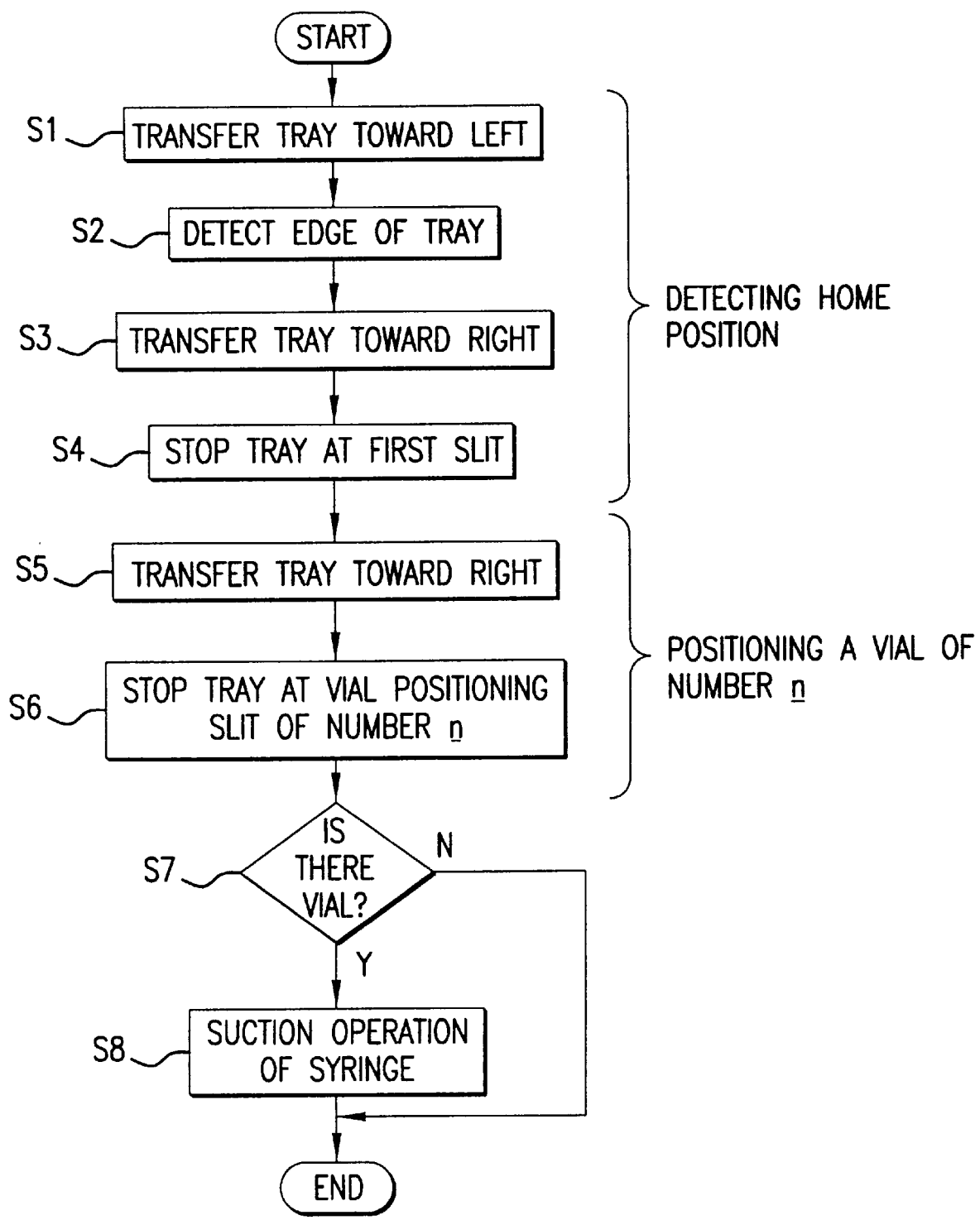
FIG. 2 is a flow chart showing operation processes of the automatic sample injection apparatus.
Figure 3A:
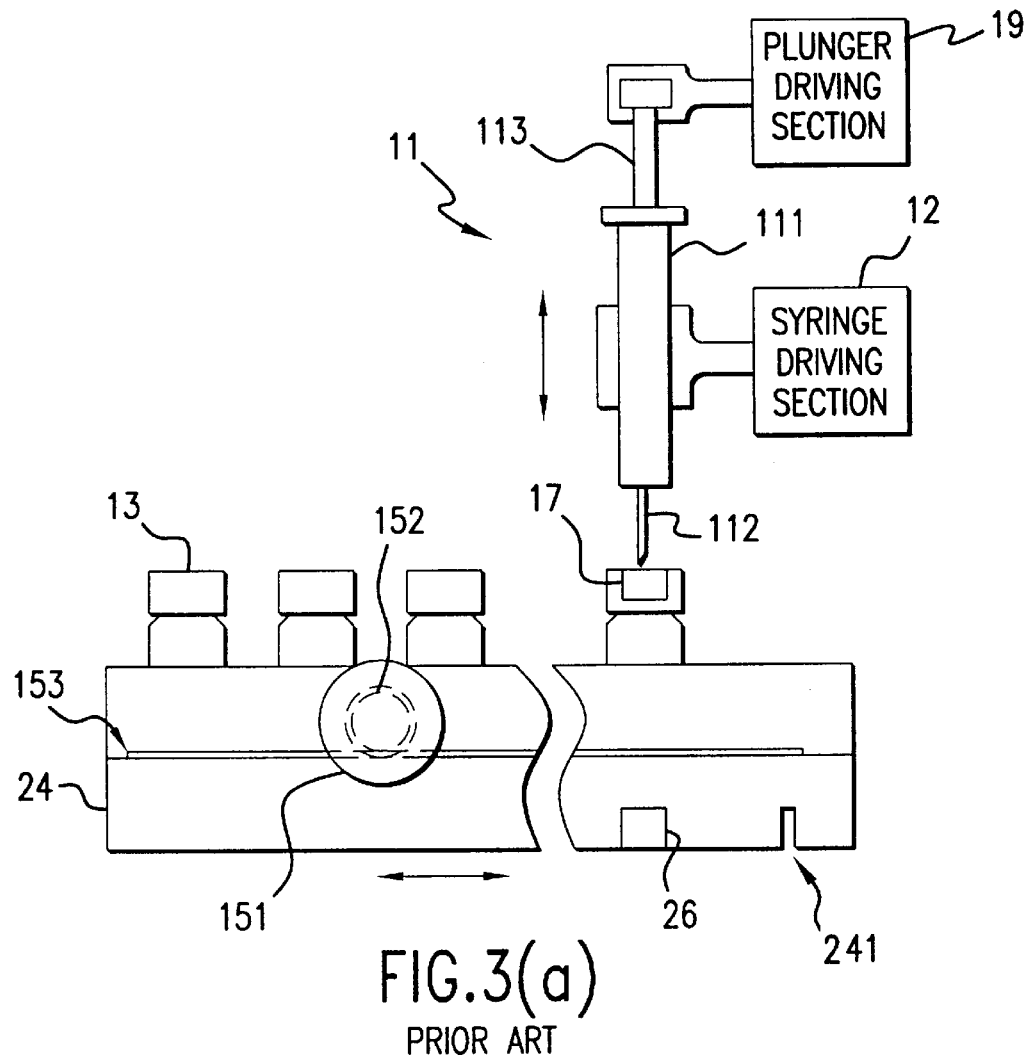
FIG. 3(a) is a front view of a conventional automatic sample injection apparatus.
Figure 3B:
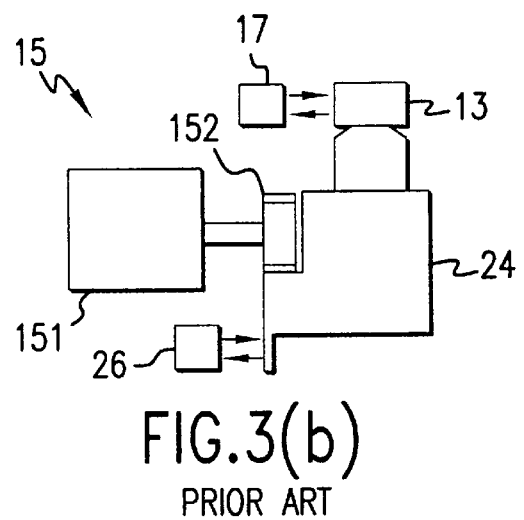
FIG. 3(b) is a side view thereof.

Hereinafter, an embodiment of the invention is explained with reference to FIGS. 1(a), 1(b) and 2. FIGS. 1(a) and 1(b) show structural views of a main part of an automatic sample treatment or injection apparatus according to the invention, and FIG. 2 is a flow chart showing operation processes of the automatic sample injection apparatus.

In the automatic sample treatment or injection apparatus 10 of the invention, in corresponding to the respective vial disposing positions in a tray 14, there are provided slits 142 (hereinafter referred to as vial positioning slits) having a shape different from that of a slit 141 (hereinafter referred to as a home position slit) for detecting a home position. Presence of the vial positioning slit 142 is detected by a vial position detecting sensor 16 which has the same structure as in the home position sensor 26 of the conventional apparatus. Namely, the vial position detecting sensor 16 has two functions, i.e. detection of the vial disposing position and detection of the home position.

Upon receiving a sensor signal of the vial position detecting sensor 16 and a sensor signal of the vial detecting sensor 17, a control section 18 controls a syringe driving section 12, a tray driving section 15, and a plunger driving section 19, described as follows.

Firstly, a pulse signal is applied to a stepping motor 151 so as to move the tray 14 toward left (step S1). Then, if it is detected that a period for which reflected light is not obtained at the vial position detecting sensor 16 lasts longer than a width a of the slit (step S2), a direction of moving the tray 14 is reversed (step S3), and the tray 14 is stopped when an edge of the first slit is detected (step S4). Accordingly, a home position slit 141 is placed at a position facing the vial position detecting sensor 16. Namely, this position is a home position, and when, for example, the syringe 11 performs operations other than the sample suction operation, e.g. injecting a sample into a sample carburetion chamber of a chromatograph apparatus, the tray 14 stands by at the home position.

Then, in case a sample is sucked from a vial 13 disposed at a sample disposing position of number n in the tray 14, the pulse signal is applied to the stepping motor 151 so as to transfer the tray 14 toward right (step S5). Then, the vial position detecting sensor 16 detects the vial positioning slits 142 and counts a number thereof, and when an edge of the vial positioning slit 142 of number n is detected, the tray 14 is stopped (step S6).

Subsequently, the vial detecting sensor 17 detects whether there is a vial 13 at the sample disposing position of number n (step S7). Then, if the presence of the vial 13 is recognized, the syringe 11 is lowered by the syringe driving section 12; and after the needle 112 is inserted into a sample inside the vial 13, a plunger 113 is pulled by the plunger driving section 19, so that a predetermined amount of the sample is sucked into the barrel 111 of the syringe 11 (step S8).

In case the presence of the vial 13 is not detected at step S7, it is determined that the vial 13 is,not placed at the sample disposing position of number n, and without performing a suction operation for the vial at the sample disposing position of number n, the process moves on to an operation of selecting a vial at a position designated as next.

Normally, the control section 18 as described above is formed of a microcomputer having CPU (Central Processing Unit) as a center thereof, and processing operations thereof are achieved by a software installed in the microcomputer. Therefore, in most cases, changes in the processing operations of the control section 18 can be adapted by merely changing and amending the software. Therefore, in regard to the conventional apparatus, the above described embodiment of the automatic sample injection apparatus can be achieved only by a change of the hardware, i.e. changing the shape of the tray 14, and a change in the software of the control section 18.

Incidentally, although the aforementioned embodiment has a structure that the slits are formed in the tray corresponding to the respective sample positions, as long as the respective sample disposing positions can be surely detected, other methods can be used. For example, it can be structured that the tray is provided with projections, and by detecting light reflected at the projections, the home position and the respective sample positions can be detected to be distinguished from each other. Also, other than using the light sensor as the vial position detecting sensor, a magnetic sensor or the like can be used as a non-contact type sensor, and furthermore, a contact type detector, such as a microswitch may be used.

Further, although the embodiment described above has a structure in which the tray 14 is linearly and slidingly transferred, the present invention can be adapted in a structure in which, for example, the tray 14 rotates along a circumference of a circle, or the tray moves along X-Y axes on a plane.

While the invention has been explained with reference to the specific embodiments of the invention, the explanation is illustrative and the invention is limited only by the appended claims.

What is claimed is:

1. An automatic sample treatment apparatus for vials, comprising:

a tray for holding a plurality of vials, said tray having vial position markers corresponding to positions where the vials are located and a home position marker for indicating a home position of the tray, said home position marker being different in shape from the vial position markers and located on the tray at a horizontal level same as that of the vial position markers, driving means connected to the tray for moving the tray and stopping the tray at a sample treatment position and a home position, position detecting means situated near the tray for detecting the vial position markers and the home position marker on the tray, vial detecting means situated near the tray for detecting a vial when the tray is stopped at the sample treatment position, a syringe disposed above the tray, and control means connected to the syringe, the position detecting means, the driving means and the vial detecting means, said control means controlling the driving means and the syringe such that the tray is moved and stopped at the home position by actuating the driving means while the home position of the tray is being detected by the position detecting means; when a vial on the tray located at a predetermined position is moved to the sample treatment position, the tray is moved and stopped by the driving means while a number of the vial position markers to the predetermined position is being counted by the position detecting means; and then if the vial detecting means detects the vial at the predetermined position, the syringe is actuated.

2. An automatic sample treatment apparatus according to claim 1, wherein each of said vial position markers is formed of a slit, said home position marker including a slit different from those of said slits for the vial position markers.

3. An automatic sample treatment apparatus according to claim 1, wherein said position detecting means is formed of a light sensor having a light emission section for emitting light and a light receiving section for receiving light reflected at the tray so that a position of the tray is detected by the light reflected at the tray.

4. An automatic sample treatment apparatus according to claim 3, wherein said syringe includes a barrel, a plunger slidably situated in the barrel and a needle attached to the barrel, said automatic sample treatment apparatus further including syringe driving means attached to the barrel for moving the barrel with the needle relative to a specific vial when the specific vial is positioned under the syringe, and plunger driving means for actuating the plunger relative to the barrel.

5. An automatic sample treatment apparatus according to claim 4, wherein said plunger driving means is actuated when the needle is inserted into a specific vial so that a sample in the specific vial is sucked into the syringe.

6. An automatic sample treatment apparatus according to claim 2, wherein said home position marker is formed of said different slit and a notch adjacent thereto.

7. An automatic sample treatment apparatus according to claim 6, wherein said detecting means provides a signal in the notch lasting longer than signals obtained at the slits of the vial position markers.

8. An automatic sample treatment apparatus according to claim 7, wherein the tray is located at the home position by moving the tray toward the home position marker, reversing a moving direction of the tray when the notch is detected by the position detecting means, and stopping the tray when the different slit is first detected by the position detecting means.

\* \* \* \* \*